United States Patent
Engler et al.

(10) Patent No.: US 7,635,091 B2
(45) Date of Patent: Dec. 22, 2009

(54) HUMIDITY SENSOR FORMED ON A CERAMIC SUBSTRATE IN ASSOCIATION WITH HEATING COMPONENTS

(75) Inventors: Kevin J. Engler, Freeport, IL (US); Michael Farrey, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 488 days.

(21) Appl. No.: 11/112,259

(22) Filed: Apr. 21, 2005

(65) Prior Publication Data

US 2006/0237551 A1 Oct. 26, 2006

(51) Int. Cl.
*G01N 19/10* (2006.01)
*G01F 1/68* (2006.01)

(52) U.S. Cl. ........................ 236/44 C; 73/29.02; 73/73; 73/204.26; 73/335.02

(58) Field of Classification Search ................ 73/29.01, 73/29.02, 23.2, 73, 204.26, 335.02; 236/44 C; 374/21
See application file for complete search history.

(56) References Cited

U.S. PATENT DOCUMENTS

| | | | |
|---|---|---|---|
| 4,330,718 A | 5/1982 | Kinomoto et al. ........... 307/118 |
| 4,386,336 A | 5/1983 | Kinomoto et al. ............. 338/35 |
| 5,040,411 A * | 8/1991 | Medzius ........................ 73/73 |
| 5,608,374 A | 3/1997 | Ikejiri ........................... 338/35 |
| 5,844,125 A * | 12/1998 | Pillion ........................ 73/29.01 |
| 6,016,686 A * | 1/2000 | Thundat ....................... 73/23.2 |
| 6,073,480 A * | 6/2000 | Gokhfeld .................... 73/29.02 |
| 6,126,311 A * | 10/2000 | Schuh .......................... 374/21 |
| 6,450,025 B1 * | 9/2002 | Wado et al. ............... 73/204.26 |
| 6,724,612 B2 | 4/2004 | Davis et al. .................. 361/328 |
| 6,836,205 B2 | 12/2004 | Scott et al. ..................... 337/3 |
| 6,840,103 B2 | 1/2005 | Lee et al. .................. 73/335.05 |
| 2002/0040598 A1* | 4/2002 | Sugaya et al. ............. 73/335.02 |
| 2003/0159928 A1* | 8/2003 | Kojima et al. ............... 204/408 |
| 2004/0233034 A1 | 11/2004 | Bernier ........................ 338/25 |
| 2004/0237646 A1 | 12/2004 | Fujita et al. .............. 73/335.05 |

* cited by examiner

*Primary Examiner*—Marc E Norman
(74) *Attorney, Agent, or Firm*—Kermit D. Lopez; Luis M. Ortiz

(57) ABSTRACT

A humidity sensor system and method include a ceramic substrate upon which a heater can be printed. A humidity sensor can be mounted above and in contact with the heater, or the heater can be mounted one side of the substrate and the humidity sensor on the opposite side of the substrate, such that the heater heats the humidity sensor, raising its temperature above the dew point of the ambient air such that moisture does not condense on the humidity sensor, thereby preventing the humidity sensor performance from being affected. The heater can be configured as a resistive heater, and the humidity sensor can be configured from one or more humidity-sensing die. A thin film platinum RTD (Resistance Temperature Detector) component can be printed upon the substrate in association with the humidity sensor.

20 Claims, 3 Drawing Sheets

HUMIDITY SENSOR FORMED ON A CERAMIC SUBSTRATE IN ASSOCIATION WITH HEATING COMPONENTS

TECHNICAL FIELD

Embodiments are generally related to sensing devices and applications. Embodiments are also related to humidity sensors and semiconductor-based sensing devices. Embodiments are additionally related to heating elements adapted for use with humidity sensors.

BACKGROUND OF THE INVENTION

Humidity sensors are utilized in a variety of sensing applications. Humidity sensors can be implemented in the context of semiconductor-based sensors utilized in many industrial applications. Solid-state semiconductor devices are found in most electronic components today. Semiconductor-based sensors, for example, are fabricated using semiconductor processes.

Many modern processes, for example, require measurement of relative humidity at dew points between −40° C. and 180° C., corresponding to relative humidity between 1% and 100%. There is a need for a durable, compact, efficient moisture detector that can be used effectively in these processes to measure very small moisture content in gaseous atmospheres.

Humidity can be measured by a number of techniques. In a semiconductor-based system, humidity can be measured based upon the reversible water absorption characteristics of polymeric materials. The absorption of water into a sensor structure causes a number of physical changes in the active polymer. These physical changes can be sensed by electrical signals which are related to the water concentration in the polymer and which in turn are related to the relative humidity in the air surrounding the polymer.

Two of the most common physical changes are the change in resistance and the change in dielectric constant, which can be respectively translated into a resistance change or a capacitance change. It has been found, however, that elements utilized as resistive components suffer from the disadvantage that there is an inherent dissipation effect caused by the dissipation of heat due to the current flow in the elements necessary to make a resistance measurement. The result is inaccuracy or erroneous readings, among other problems.

Elements constructed to approximate a pure capacitance avoid the disadvantages of the resistive elements. It is important in the construction of capacitive elements, however, to avoid the problems that can arise with certain constructions for such elements. In addition, there can also be inaccuracy incurred at high relative humidity values where high water content causes problems due to excessive stress and the resulting mechanical shifts in the components of the element. By making the component parts of the element thin, it has been found that the above-mentioned problems can be avoided and the capacitance type element can provide a fast, precise measurement of the relative humidity content over an extreme range of humidity as well as over an extreme range of temperature and pressure and other environmental variables.

Humidity-sensing elements of the capacitance sensing type usually include a moisture-insensitive, non-conducting substrate structure with appropriate electrode elements mounted or deposited on the structure along with a layer or coating of dielectric, highly moisture-sensitive material overlaying the electrodes and positioned so as to be capable of absorbing water from the surrounding atmosphere and reaching equilibrium in a short period of time. Capacitive humidity sensors are typically constructed by depositing several layers of material on a substrate material. An example of a humidity sensor is disclosed in U.S. Pat. No. 6,724,612, entitled "Relative Humidity Sensor with Integrated Signal Conditioning," which issued to Davis et al on Apr. 20, 2004, and issued to Honeywell International, Inc. U.S. Pat. No. 6,724,612 is incorporated herein by reference.

One of the problems with conventional humidity sensors is that such devices are continually plagued with inaccurate output due to disruption of the sensing polymer from condensation. A need exists for configuring and providing heated humidity sensor structures with components of similar material construction and size for improved heat conduction thus resulting low power heating capability. It is believed that the embodiments disclosed herein provide for such capabilities.

BRIEF SUMMARY OF THE INVENTION

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

It is, therefore, one aspect of the embodiments to provide for improved sensing devices and applications.

It is another aspect of the embodiments to provide for humidity sensors and semiconductor-based sensing devices.

It is a further aspect of the embodiments to provide for improved heating elements adapted for use with humidity sensors.

It is an additional aspect of the embodiments to provide for a humidity-sensing device that incorporate resistance temperature detectors (RTDs) in association with capacitive humidity sensing elements and resistive heating components.

It is yet a further aspect of the embodiments to provide for a humidity-sensing device formed from a ceramic substrate.

The aforementioned aspects and other objectives and advantages can now be achieved as described herein. Humidity sensor systems and methods thereof are disclosed. In general, a ceramic substrate can be provided and a heater thereafter printed upon the ceramic substrate. A humidity sensor can be then mounted immediately above and in contact with the heater, such that the heater heats the humidity sensor, raising its temperature above the ambient dew point such that moisture does not condense on the humidity sensor, thereby preventing the humidity sensor performance from being affected. The heater can be configured as a resistive heater, and the humidity sensor can be configured from one or more humidity-sensing die or elements.

In accordance with a preferred embodiment, a humidity sensor system and/or method can be implemented in which a ceramic substrate is provided and a heater configured upon a first side of the substrate. A humidity sensor can then be mounted on a second side of the substrate opposite the first side, wherein the heater heats the humidity sensor, raising its temperature above the ambient dew point such that moisture does not condense on the humidity sensor, thereby preventing the humidity sensor performance from being affected.

The heater can be printed upon the substrate and implemented as a resistive heater. The humidity sensor can be composed of one or more humidity-sensing elements, which are preferably formed as capacitive humidity-sensing elements. Finally, a thin film platinum RTD (Resistance Temperature Detector) component can be printed upon the first side of the substrate in association with the humidity sensor. The thin film platinum RTD component can be utilized to sense the surface temperature of the sensor body formed from the ceramic substrate, thereby providing feedback for a control circuit.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
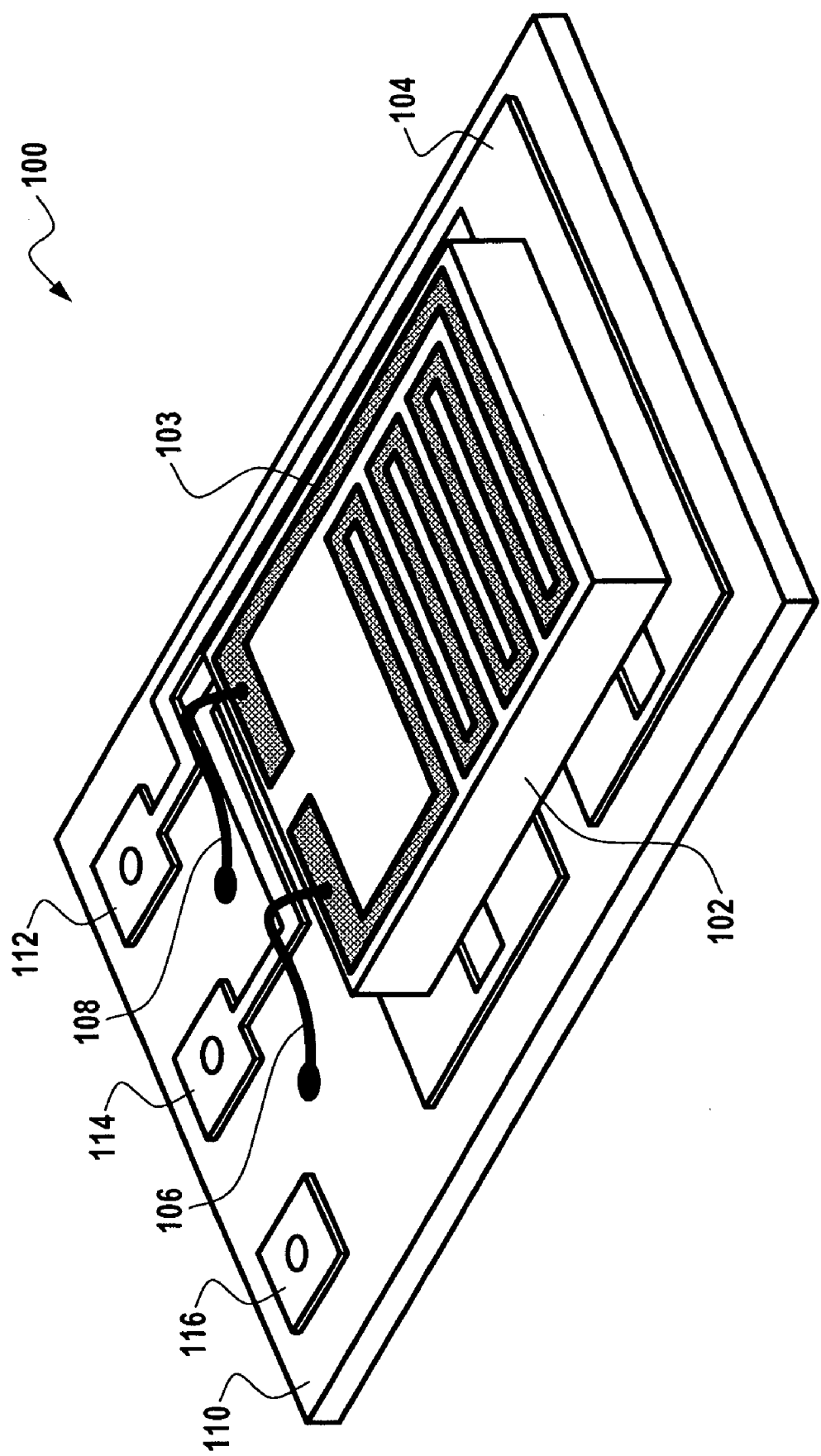
FIG. 1 illustrates a perspective view of a humidity sensor system that includes a ceramic heater associated with a ceramic substrate humidity sensor mounted above one or more heater traces in accordance with one embodiment.

FIG. 1 illustrates a perspective view of a humidity sensor device or system 100 that includes a ceramic heater 110 associated with a ceramic humidity sensor 103 mounted above one or more heater traces 104 in accordance with one embodiment. Printed resistive heating element 104 is utilized to heat humidity sensor substrate 102 and thereby raise its temperature above the ambient dew point such that moisture does not condense on the humidity sensing element 103. System 100 generally incorporates a structure in which a resistive printed heater is printed on a ceramic substrate 110 in order to form a ceramic heater. The electrical connections of ceramic substrates 110 and 102 can be over-coated for protection and robustness. Ceramic humidity sensor 103 can be configured to include one or more humidity-sensing die and can be configured in the context of an ultra H humidity sensor. A plurality of electrical components or contacts 116, 114, 112 can also be provided with system 100 in addition to electrical connections 106 and 108.

Figure 2:
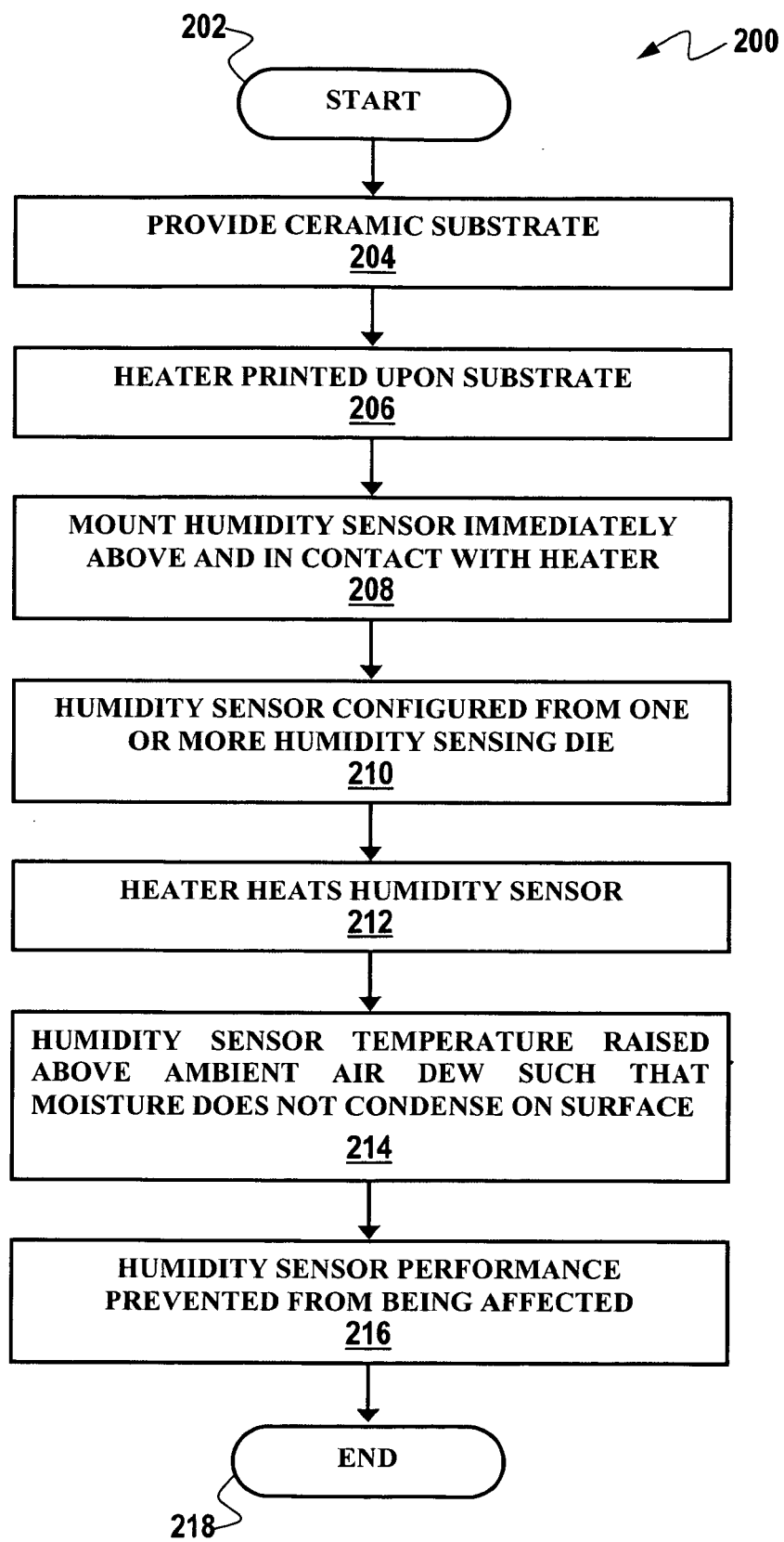
FIG. 2 illustrates a high-level flow chart outlining a methodology for configuring and operating a humidity sensor in accordance with an embodiment.

FIG. 2 illustrates a high-level flow chart 200 outlining a methodology for configuring and operating a humidity sensor, such as the humidity sensor system 100 depicted in FIG. 1 in accordance with one embodiment. As indicated at block 202, the process can be initiated. Thereafter, as illustrated at block 204, a ceramic substrate can be provided. Next, as described at block 206, a heater can be configured upon the ceramic substrate. The heater itself can be provided as a resistive heater. As indicated next at block 208, the humidity sensor can be mounted above and in contact with the heater. Note that the humidity sensor can be configured from one or more humidity-sensing die, as depicted at block 210. The actual operation of the humidity sensor (e.g., humidity sensor 100) can be implemented as indicated at block 212-216. As illustrated at block 212, the heater can heat the humidity sensor. Thereafter, as depicted at block 214, the temperature of the humidity sensor is raised above the ambient dew point such that the moisture does not condense on the sensor surface. Thus, the moisture in the associated air does not condense on the humidity sensor, thereby preventing the humidity sensor performance from being adversely affected as indicated at block 216. The process can thereafter terminate as described at block 218.

Figure 3:
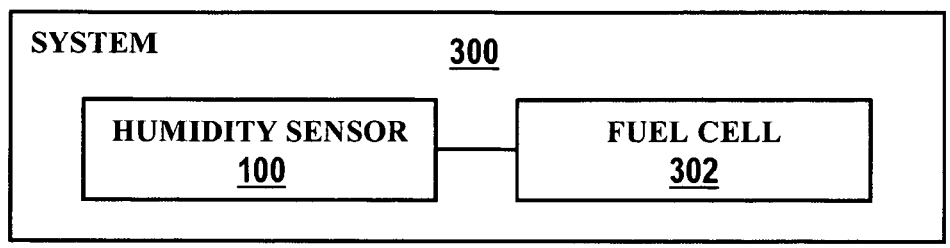
FIG. 3 illustrates a humidity-sensing system, which can be implemented in accordance with another embodiment.

FIG. 3 illustrates a humidity-sensing system 300, which can be implemented in accordance with an alternative embodiment. Note that in FIGS. 1-3, identical or similar parts or elements are generally indicated by identical reference numerals. System 300 can be configured for use in detecting humidity involved in hydrogen fuel cell operations. Thus, system 300 includes humidity sensor 100, which is connected to and/or communicates directly with fuel cell 302. Note that system 300 illustrates one possible alternative embodiment, which can be modified depending upon design considerations. For example, the sensing system 400 described herein can be implemented in place of humidity sensor 100.

System 300 can be applied to a number of important industrial and commercial applications. One significant application of humidity sensor 100 can involve fuel cell applications. There are several kinds of fuel cells, but Polymer Electrolyte Membrane (PEM) fuel cells—also called Proton Exchange Membrane fuel cells—are the type typically used in automobiles. Fuel cell 302 can be implemented, for example, as a PEM fuel cell. A PEM fuel cell uses hydrogen fuel and oxygen from the air to produce electricity. In general, most fuel cells designed for use in vehicles produce less than 1.16 volts of electricity, which is usually not sufficient to power a vehicle. Therefore, multiple cells must be assembled into a fuel cell stack. The potential power generated by a fuel cell stack depends on the number and size of the individual fuel cells that comprise the stack and the surface area of the PEM.

One example of a fuel cell application that can be utilized to implement fuel cell 302 is disclosed in U.S. Pat. No. 6,607,854, "Three-Wheel Air Turbocompressor for PEM fuel Cell Systems," and issued to Rehg et al. on Aug. 19, 2003. U.S. Pat. No. 6,607,854 discloses a fuel cell system comprising a compressor and a fuel processor downstream of the compressor. In U.S. Pat. No. 6,607,854, a fuel cell stack is configured in communication with the fuel processor and compressor. A combustor is downstream of the fuel cell stack. First and second turbines are downstream of the fuel processor and in parallel flow communication with one another. A distribution valve is in communication with the first and second turbines. The first and second turbines are mechanically engaged to the compressor. A bypass valve is intermediate the compressor and the second turbine, with the bypass valve enabling a compressed gas from the compressor to bypass the fuel processor. U.S. Pat. No. 6,607,854 is assigned to Honeywell International, Inc., and is incorporated herein by reference.

Another example of a fuel cell application which can be utilized to implement fuel cell 302 is disclosed in U.S. Patent Publication No. 2003/0129468A1, "Gas Block Mechanism for Water Removal in Fuel Cells" to Issacci et al., which was published on Jul. 10, 2003 and is assigned to Honeywell International, Inc. U.S. Patent Publication No. 2003/0129468A1 is incorporated herein by reference. A further example of a fuel cell application which can be utilized to implement fuel cell 302 is disclosed in U.S. Patent Publication No. 2003/0124401A1, "Integrated Recuperation Loop in Fuel Cell Stack" to Issacci et al., which was published on Jul. 3, 2003 and is assigned to Honeywell International, Inc. U.S. Patent Publication No. 2003/0124401A1 is also incorporated herein by reference.

Figure 4:
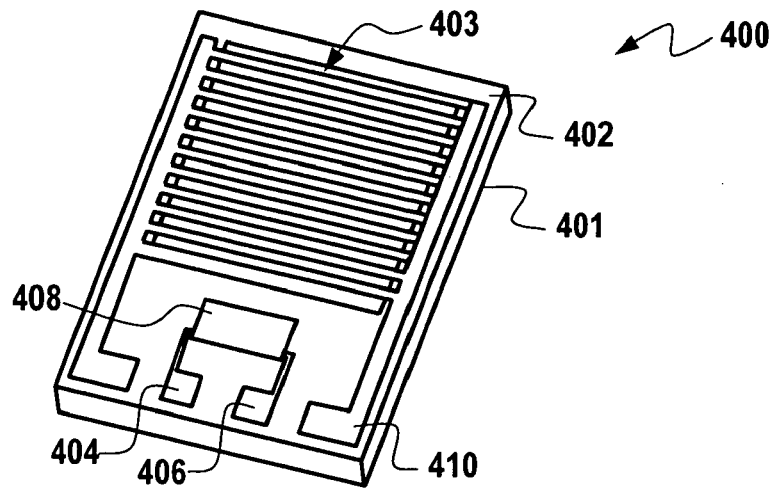
FIG. 4 and FIG. 5 illustrate a humidity-sensing system, which can be implemented in accordance with a preferred embodiment.
Figure 5:
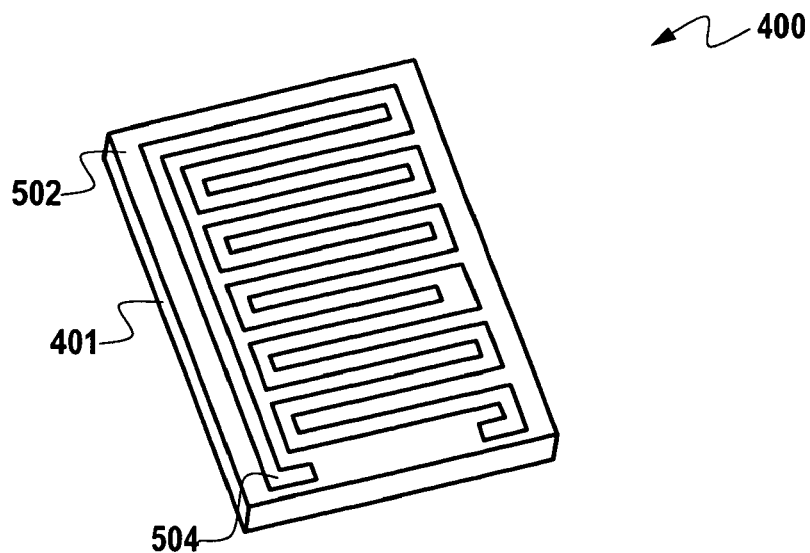

FIG. 4 and FIG. 5 illustrate a humidity-sensing system 400, which can be implemented in accordance with a preferred embodiment. In FIG. 4, a sensing side 402 of system 400 is illustrated, while in FIG. 5, a backside of system 400 is depicted. Sensing side 402 generally includes a capacitive humidity element 403 in association with one or more thin film platinum RTD components 408 and electrical connection points 404, 406 and 410, while the back side 502 incorporates a printed resistive heating element 504 thereon. In general, system 400 includes a substrate 401 and a heater or printed resistive heating element 504 configured upon substrate 401. Substrate 401 is preferably formed ceramic.

System 400 generally functions as a humidity sensor composed of the capacitive humidity element 403, the thin film platinum RTD (Resistance Temperature Detector) component 408, electrical connection points 404, 406 and 410, and the printed resistive heating element 504 (i.e., heater) contained in one entity. The capacitive humidity element 403 and the thin film platinum RTD component 408, and electrical connection points 404, 406 and 410 are printed onto the ceramic substrate 401 with the resistive heating element 504 being printed on the opposite side.

Note that a resistance temperature detector (RTD) is essentially a sensing element that works on the principle of the temperature coefficient of the electrical resistance of metals. Thus, thin film platinum RTD component 408 provides a change in resistance proportional to a change in temperature. A known electrical current passed through the RTD component 408 can produce a voltage drop across the RTD component 408. This voltage drop can then be measured by a calibrated device (not shown in FIG. 4) to determine the temperature change. RTD component 408 can be utilized to monitor a temperature at a particular point.

The resistive heating element 504 is utilized to raise the temperature of the sensor body (i.e., system 500) above the ambient dew point such that moisture does not condense onto the humidity-sensing element 504. The thin film platinum RTD component 408 is utilized to sense the surface temperature of the sensor body providing feedback for a control circuit. Note that system 400 depicted in FIG. 4 can be adapted for use with system 300 depicted in FIG. 3. For example, instead of utilizing humidity sensor 100, system 300 can be modified to utilize system 400 (i.e., humidity sensor) in place of humidity sensor 100.

Examples of possible RTD components that can be adapted for use with the preferred embodiment is disclosed in U.S. Pat. No. 6,836,205, "Thermal Switch Containing Resistance Temperature Detector," which issued to Scott et al on Dec. 28, 2004 and is assigned to Honeywell International Inc. U.S. Pat. No. 6,836,205 is incorporated herein by reference and disclosed. Another example of an RTD component that can be adapted for use with the preferred embodiment is the HEL-700 thin film platinum RTD produced by Honeywell International Inc. The HEL-700 thin film platinum RTD provides for an enhanced linearity, accuracy, stability and interchangeability. The HEL-700 thin film platinum RTD provides for resistance that changes linearly with temperature. It can be appreciated that such RTD components are referred to herein for general edification and illustrative purposes only and are not considered limiting features of the embodiments.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A humidity sensor system, comprising:
   a first substrate and an independent second substrate;
   a heating element printed on said first substrate, wherein said independent second substrate is mounted in direct contact with said first substrate, such that said first substrate, said independent second substrate and said heating element form a humidity sensor that provides heated humidity sensor operations with temperature feedback information thereof.

2. The system of claim 1 wherein said heating element heats said humidity sensor in order to raise a temperature of said humidity sensor above a dew point of associated air such that moisture does not condense on said humidity sensor, thereby preventing a performance of said humidity sensor from being affected.

3. The system of claim 1 further comprising at least one resistance temperature detector (RTD) component printed upon said independent second substrate in association with said humidity sensor in order to sense a surface temperature of said sensor body.

4. The system of claim 3 wherein said at least one RTD component comprises a thin film platinum RTD component.

5. The system of claim 1 wherein said first and independent second substrates comprise ceramic.

6. A humidity sensor system, comprising:
   a substrate;
   a humidity-sensing element printed on the surface of a side of said substrate;
   at least one RTD component printed on the surface of said side of said substrate upon which said humidity-sensing element is printed;
   a heating element printed on the surface of a side of said substrate opposite said side of said substrate upon which said humidity-sensing element and said at least one RTD component are printed, wherein said substrate, said humidity-sensing element and said heating element form a humidity sensor that provides heated humidity sensor operations with temperature feedback information thereof.

7. The system of claim 6 wherein said heating element heats said humidity sensor in order to raise a temperature of said humidity sensor above a dew point of associated air such that moisture does not condense on said humidity sensor, thereby preventing a performance of said humidity sensor from being affected.

8. The system of claim 6 wherein said at least one RTD component is printed upon the surface of said side of said substrate upon which said humidity-sensing element is printed in order to sense a surface temperature of said humidity sensor.

9. The system of claim 8 wherein said at least one RTD component comprises a thin film platinum RTD component.

10. The system of claim 6 wherein said substrate comprise ceramic.

11. A humidity sensing method, comprising:
providing a first substrate and an independent second substrate;
printing a heating element on said first substrate; and
mounting said independent second substrate in direct contact with said first substrate, such that said first substrate, said independent second substrate and said heating element form a humidity sensor that provides heated humidity sensor operations with temperature feedback information thereof.

12. The method of claim 11 wherein said heating element heats said humidity sensor in order to raise a temperature of said humidity sensor above a dew point of associated air such that moisture does not condense on said humidity sensor, thereby preventing a performance of said humidity sensor from being affected.

13. The method of claim 11 further comprising at least one resistance temperature detector (RTD) component printed upon said independent second substrate in association with said humidity sensor in order to sense a surface temperature of said sensor body.

14. The method of claim 13 further comprising configuring said at least one RTD component to comprise a thin film platinum RTD component.

15. The method of claim 11 further comprising providing said first and independent second substrates as ceramic.

16. A humidity sensor method, comprising:
providing a substrate;
printing a humidity-sensing element on the surface of a side of said substrate;
printing at least one RTD component on the surface of said side of said substrate upon which said humidity-sensing element is printed; and
printing a heating element on the surface of a side of said substrate opposite said side of said substrate upon which said humidity-sensing element and said at least one RTD component are printed, wherein said substrate, said humidity-sensing element and said heating element form a humidity sensor that provides heated humidity sensor operations with temperature feedback information thereof.

17. The method of claim 16 wherein said heating element heats said humidity sensor in order to raise a temperature of said humidity sensor above a dew point of associated air such that moisture does not condense on said humidity sensor, thereby preventing a performance of said humidity sensor from being affected.

18. The method of claim 16 wherein said at least one RTD component is printed upon the surface of said side of said substrate upon which said humidity-sensing element is printed in order to sense a surface temperature of said humidity sensor.

19. The method of claim 18 further comprising configuring said at least one RTD component to comprise a thin film platinum RTD component.

20. The method of claim 16 wherein further comprising providing said substrate as ceramic.

* * * * *

UNITED STATES PATENT AND TRADEMARK OFFICE
CERTIFICATE OF CORRECTION

PATENT NO. : 7,635,091 B2  Page 1 of 1
APPLICATION NO. : 11/112259
DATED : December 22, 2009
INVENTOR(S) : Engler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 680 days.

Signed and Sealed this

Ninth Day of November, 2010

David J. Kappos
*Director of the United States Patent and Trademark Office*